United States Patent [19]

Levy et al.

[11] 4,036,899

[45] July 19, 1977

[54] SYNTHESIS OF PRENYL CHLORIDE

[75] Inventors: Joseph Levy, Northbrook; Nils J. Christensen, Palatine, both of Ill.

[73] Assignee: UOP Inc., Des Plaines, Ill.

[21] Appl. No.: 650,813

[22] Filed: Jan. 20, 1976

[51] Int. Cl.² .............................................. C07C 21/00
[52] U.S. Cl. ................................................ 260/654 R
[58] Field of Search .................................... 260/654 R

[56] References Cited

U.S. PATENT DOCUMENTS 3,055,954    9/1962    Montagna et al. ............... 260/654 R

FOREIGN PATENT DOCUMENTS 124,000    8/1967    Czechoslovakia ............... 260/654 R
1,548,516  10/1968   France .............................. 260/654 R
855,696   12/1960   United Kingdom ............ 260/654 R Primary Examiner—Delbert E. Gantz
Assistant Examiner—Joseph A. Boska
Attorney, Agent, or Firm—James R. Hoatson, Jr.; Raymond H. Nelson; William H. Page, II

[57] ABSTRACT

Prenyl chloride (1-chloro-3-methylbutene-2) may be synthesized in increased yields by reacting isoprene with hydrochloric acid in the presence of sodium chloride. In addition, the yield may also be advantageously increased by utilizing a modified method of operation in which the distillation heads and tails fractions which are obtained from the process are recycled to the reaction zone.

9 Claims, No Drawings

SYNTHESIS OF PRENYL CHLORIDE

BACKGROUND OF THE INVENTION

Prenyl chloride is an important intermediate in the preparation of valuable aroma chemicals such as linalool, geraniol, citronellol as well as many aroma chemicals which are derived from these compounds. The thus prepared aroma products are themselves useful as components when compounding fragrant compositions of matter which are useful in the cosmetic or toiletry industry, said compositions being useful in perfumes, colognes, talcum powders, soaps, detergents, bath powders, etc. The prior art teaches procedures in which isoprene is reacted with anhydrous hydrogen chloride or aqueous concentrated hydrochloric acid. Generally speaking there are two methods which may be utilized in the preparation of the desired compound. One method involves effecting the reaction at temperatures below about 0° C. with the attendant formation of the tertiary chloride derivative, namely, 3-chloro-3-methylbutene-1. Thereafter the temperature is raised to about 0° C. to a range of from about 10° to 30° C. whereby the tertiary chloride product is isomerized to form 1-chloro-3-methylbutene-2 (prenyl chloride). Alternatively, the treatment of isoprene with hydrochloric acid or hydrogen chloride can be conducted at higher temperatures ranging from about 0° to produce about 20° C. to produce the prenyl chloride in a direct manner. For example, Britist Pat. No. 855,696 discloses the treatment of isoprene with concentrated aqueous hydrochloric acid at temperatures ranging from 10° to 15° C. However, the yield which is disclosed is 63% of prenyl chloride which distills over a 7° range of from 106° to 113° C. In addition, there is also present 8% of the tertiary chloride compound. Another prior art reference, French Pat. No. 1,548,516, discloses the treatment of isoprene with concentrated hydrochloric acid and concentrated sulfuric acid at a temperature of 30° C. In this instance there has been reported an 80% total yield of product consisting of 29.5% of unreacted isoprene, 6.8% of the tertiary chloride and only 57% of the desired compound, namely, prenyl chloride. Another prior art reference for the preparation of prenyl chloride is F. K. Sngryan et al, Arm. Khim. Zh., 26, 563 (1973) in which a 92% selectivity of prenyl chloride is reported at 20° C. but only at a 50–55% conversion of isoprene. In general, the results reported in the other processes of prior art are of about the same order of magnitude as cited in the above.

In contradistinction to the methods which are set forth in the prior art, we have now discovered that by treating isoprene with concentrated hydrochloric acid as the hydrohalogenating reagent in the presence of an alkali or alkaline earth metal chloride compound and, in an advantageous manner, in the presence of the by-product heads and tails fractions obtained from the distillation of a prior reaction involving the same compounds, it is possible to obtain high yields of prenyl chloride with a high selectivity of the desired compound and a high conversion of isoprene.

This invention relates to a process for the synthesis of prenyl chloride. More specifically, the invention is concerned with a process for the synthesis of prenyl chloride which involves treating isoprene with hydrochloric acid in the present of an alkali or alkaline earth metal chloride compound whereby a high conversion and selectively of the starting material and product is obtained plus an excellent purity of the product.

As hereinbefore set forth, a prenyl chloride, which also may be nomenclated as 1-chloro-3-methylbutene-2, is a valuable intermediate for the synthesis of terpenoid alcohols such as linalool, geraniol, citronellol, etc., the latter compounds forming components of aromatic compositions of matter. It is a desired feature of the process for the synthesis of prenyl chloride that the product be obtained in relatively high yields with a correspondingly high purity of the product. This high purity of the product is a necessary feature inasmuch as many impurities which may be present must be removed by costly distillation methods in order that the product may be utilized in the further formation of aroma chemicals which possess distinctive and desired fragrances. By utilizing the process of this invention, it is possible to attain these ends.

It is therefore an object of this invention to provide a process for the synthesis of prenyl chloride.

A further object of this invention is to provide a process for the preparation of prenyl chloride by treating isoprene with a hydrogen chloride compound in the presence of an alkali or alkaline earth metal chloride compound whereby the desired product is obtained in a high yield and will possess a high purity.

In one aspect an embodiment of this invention resides in a process for the preparation of prenyl chloride which comprises reacting isoprene with hydrochloric acid in the presence of an alkali metal chloride at reaction conditions, and recovering the resultant prenyl chloride.

A specific embodiment of this invention if found in a process for the preparation of prenyl chloride which comprises reacting isoprene with concentrated hydrochloric acid in the presence of sodium chloride at a temperature in the range of from 0° to about 30° C., and recovering the resultant prenyl chloride.

Other objects and embodiments will be found in the following further detailed description of the present invention.

As hereinbefore set forth in greater detail, the present invention is concerned with an improvement in the process for synthesizing prenyl chloride, said improvement resulting in the obtention of greater yields of purer product with correspondingly high percentage of selectivity. As opposed to many prior art processes which utilized gaseous or anhydrous hydrogen chloride, the present invention permits the use of concentrated aqueous hydrochloric acid which is less expensive reagent than is the anhydrous hydrogen chloride. In addition, the use of the concentrated aqueous hydrochloric acid will permit a less complicated operating procedure to be employed. The synthesis of prenyl chloride according to the process of the present invention is effected by treating isoprene with aqueous concentrated hydrochloric acid and preferably a 37% concentrated hydrochloric acid solution although 32% acid may be used if desired. The improvement in the process lies in the presence of an inorganic chloride compound selected from the group consisting of alkali metal and alkaline earth metal chlorides. Specific examples of these chlorides will include solium chloride, potassium chloride, lithium chloride, rubidium chloride, cesium chloride, magnesium chloride, calcium chloride, strontium chloride, barium chloride, etc., the preferred chloride compounds comprising sodium chloride and potassium chloride and especially sodium chloride due to their relatively greater availability and correspondingly lower cost. In the preferred embodiment of the invention, the hydrochloric acid is present in a molar excess in a range of from about 1.1 to about 2.5 moles of hydrochloric acid per mole of isoprene. Generally speaking the hydrochloric acid and the sodium chloride are preferably added in an incremental manner to the reaction vessel during the reaction time which may range about 0.5 to about 10 hours or more in duration. The concentrated hydrochloric acid and the sodium chloride in solid form may be added separately or, if so desired, the sodium chloride and hydrochloric acid may be admixed prior to being added to the reactor and the resultant mixture is then charged thereto in a single stream. By utilizing an alkali chloride compound such as sodium chloride, a saturated solution of the aqueous phase will be maintained during the course of the reaction thus facilitating the transfer of the hydrogen chloride from the aqueous phase to the organic phase. The treatment of the isoprene with the hydrochloric acid and the alkali metal chloride is accomplished at temperatures ranging from subambient (about 0° C.) up to about 30° C. or more, thus permitting the direct synthesis of prenyl chloride (1-chloro-3-methylbutene-2) rather than first forming the tertiary chloride compound (3-chloro-3-methylbutene-1) which must then be isomerized to form the desired compound.

In another embodiment of the invention, it is contemplated that the treatment of the isoprene with the hydrochloric acid and inorganic chloride compound may also be advantageously effected in the presence of byproduct heads and tails fractions which had been obtained from the distillation of the product according to a prior run. By recycling the heads and tails fractions from the distillation, it has been found that the formation of the tertiary chloride compound is minimized over the amount which was produced during the previous run. Likewise, it has also been found that the presence of the inorganic chloride compound also reduces the formation of 2,4-dichloro-2-methylbutane as well as the amount of heavies which have formed during the previous run. The advantage of utilizing the presence of the byproduct heads and tails fractions to produce the desired result will be graphically illustrated in the examples at the end of the specification.

As hereinbefore set forth, by utilizing the presence of an alkali metal chloride compound such as sodium chloride as well as in the presence of heads and tails fractions from a preceding distillation for the recovery of prenyl chlorides, it is possible to effect the reaction in either a batch or continuous manner of operation. For example, when a batch type operation is used, in one embodiment of the invention, a predetermined amount of isoprene is placed in a suitable reactor vessel along with, if so desired, the byproduct heads and tails materials from the distillation of a previous reaction. The reactor vessel is maintained at a predetermined temperature level which may range from about 0° to about 10° C. Thereafter the concentrated hydrochloric acid in a 37% concentration and solid alkali metal chloride such as sodium chloride are added in incremental portions during a period of about 2 hours. As hereinbefore set forth, the hydrochloric acid and solid sodium chloride may be added in separate streams or, if so desired, they may also be admixed prior to entry into said reactor vessel and the resulting mixture charged thereto in a single stream. At the end of the 2-hour period, during which moderate stirring is effected, the temperature of the reactor, which may be controlled by means of any external cooling means known in the art, is raised to a range of from about 15° to about 20° C. and maintained in this range for an additional period of 3 hours. At the end of the 3-hour period, the temperature is then lowered to about 0° to 5° C. and the bottom aqueous layer is separated from the organic layer after mixing is discontinued and discarded. The organic layer is then treated with a suitable alkaline drying agent such as sodium carbonate, potassium carbonate, lithium carbonate, calcium carbonate, etc., whereby the product is dried and, in addition, any hydrogen chloride which is dissolved therein will be neutralized. Following this, the organic layer is separated from the drying agent by filtration, decantation, etc., and subjected to fractional distillation, preferably under reduced pressure whereby the desired prenyl chloride is separated and recovered. The heads and tails fractions from this distillation may then be recycled and added to fresh isoprene in a subsequent run which is effected in a similar manner to that just described. By repeatedly recycling the byproducts comprising the heads and tails materials from one run to the next plus the addition of an alkali metal chloride to the reaction system, an approximately steady state system is achieved which will afford a relatively high yield of the desired product with a concurrent diminution of undesired tertiary chloride products such as 3-chloro-3-methylbutene-1, dichloro-substituted products such as 2,4-dichloro-2-methylbutane, and other heavies. These advantages will be hereinafter shown in greater detail in the examples which are appended to the specification.

It is also contemplated within the scope of this invention that the process for obtaining improved yields of prenyl chloride may also be effected in a continuous manner of operation. When such a type of operation is employed, a quantity of isoprene is continuously charged to a reactor vessel which is maintained at the proper operating conditions of temperature and pressure. In like manner, a mixture of the concentrated hydrochloric acid and an alkali metal chloride compound such as sodium chlorode admixed therein is intermittently charged to the reaction vessel at a predetermined rate over a predetermined period of time whereby said isoprene is treated with hydrochloric acid to form the desired prenyl chloride. In addition, heads tails materials which are obtained from a distillation of already formed product are also recovered from the distillation apparatus and charged to the reactor vessel concurrently with the isoprene. After completion of the desired residence time, the reactor effluent is continuously withdrawn and the product isolated as in the above-described batch process and passed to a distillation apparatus whereby the desired prenyl chloride is separated and recovered while the aforesaid heads and tails materials are recycled to form a portion of the feed stock.

In addition to the aforementioned steps of preparing and recovering the desired prenyl chloride, it is also comtemplated within the scope of this invention that the distillation of the product of the reaction may be effected over anhydrous alkaline metal carbonates such as sodium carbonate, potassium carbonate, lithium carbonate, etc., which will act as a stabilizer and prevent decomposition of the material during the distillation step.

The following examples are given to illustrate the process of the present invention. However, it is to be understood that these examples are set forth merely for the purpose of illustration and it is not intended to limit the generally broad scope of the present invention in strict accordance therewith.

EXAMPLE 1

In this example 1,020 grams (15 moles) of isoprene was placed in a 5 liter flask which was cooled to a temperature of about 0° C. The isoprene was stirred and 2510 milliliters, 2,962 grams (30 moles) of concentrated aqueous hydrochloric acid having a concentration of 37% was slowly added thereto at a rate of about 1250 cc per hour. After a period of about 10 minutes had elapsed, 30 grams of solid chloride was added to the mixture and additional amounts of 30 grams of solid sodium chloride were added in incremental portions every 10 minutes for a period of 2 hours. During the 2-hour reaction period, the temperature of the reactor was maintained in a range of from 0° to 10° C. At the end of the 2-hour period, when 350 grams of sodium chloride (6.84 mole) had been added, the temperature of the bath was allowed to increase to about 14° C. in order to complete the reaction. Thereafter the reaction mixture was maintained at a temperature of from about 10° to about 15° C. for an additional period of 3 hours following which the contents of the reaction vessel were cooled to 5° C. and transferred to a separatory funnel. After separation of the two layers had occurred, the aqueous layer was drawn off and the desired reaction product comprising 1465 grams of a clear yellow solution was treated with 200 grams of anhydrous sodium carbonate to remove any water which may still have been present as well as neutralize any dissolved hydrogen chloride which may have been present. The product was then decanted and subjected to fractional distillation under reduced pressure over anhydrous potassium carbonate and the heart cuts boiling from 73° to 75° C. at a pressure of from about 220 to 224 mm of mercury were recovered. The analysis of these cuts was made on a gas-liquid chromatographic instrument. In addition, the heads fraction which has a vapor temperature boiling range of from 43°-73° C. at reduced pressure of from about 280 to 225 mm was recovered as well as the tails and heavies material, the latter two boiling from 76°-79° C. at reduced pressure of from about 222-147 mm. Analysis of the products determined that there had been a 93% conversion of the isoprene charged with a 75% yield of prenyl chloride.

EXAMPLE II

In this example 204 grams (3.0 mole) of isoprene plus 84 grams of combined heads and tails fractions from the previous distillation of a similar reaction which comprised 2.5 grams of isoprene, 23.2 grams of 3-chloro-3-methylbutene-1, 11.5 grams of prenyl chloride, 12.7 grams of 2,4-dichloro-2-methylbutane and 4.3 grams of intermediate cuts along with 29.9 grams of cyclohexane, which had been used to extract adhering product from the sodium carbonate drying agent, were charged to a reaction flask provided with a stirrer, thermometer, condenser, and two addition funnels, one for liquid and the other solid. The reaction flask was cooled to subambient temperature of about 0°-5° C. and 592 grams (6 moles) of a 37% concentrated hydrochloric acid was gradually added with moderate stirring during a period of 2 hours while maintaining the temperature of the reaction flask in a range of from about 2° to 9° C. In addition, 70 grams (1.2 mole) of sodium chloride was added in approximately equal portions at intervals of about 15 minutes concurrently with the addition of the hydrochloric acid. At the end of the 2-hour period, the reaction flask was warmed to a temperature of about 15° C. and maintained thereat for an additional period of 3 hours, following which the flask was again cooled to a range of from 0° to 5° C. The reaction mixture was transferred to a separatory funnel and after separation had occured, the bottom aqueous layer was withdrawn and discarded. The upper organic layer was treated with 45 grams of anhydrous sodium carbonate to remove any traces of water which may still have been present as well as neutralizing any dissolved hydrogen chloride contained therein. The organic layer was decanted to separate it from the sodium carbonate and the latter washed with 30 grams of cyclohexane to remove any adhering products. The combined product and washes were distilled over anhydrous potassium carbonate under reduced pressure, there being recovered 3 main distillation fractions at pressures varying from about 273 mm to 130 mm with corresponding vapor temperatures from about 30° to about 91° C. The fractions were analyzed on an integrator equipped gas-liquid chromatographic instrument. These analyses determined that there had been an 86% conversion of isoprene with an 89% selectivity to prenyl chloride. The weight percent of heavies which generated by the run was only 2.5% which compared to 4% heavies in the preceding run. In addition, only 1.4% of tertiary chloride compound was present compared to 8% obtained in a comparable run utilizing no recycle material.

EXAMPLE III

To illustrate the advantages of utilizing the presence of heads and tails fractions from previous distillations in the reaction mixture to minimize the formation of tertiary chloride compounds as well as heavies with the concurrent presence of an alkali metal chloride compound, such as sodium chloride, series of reactions were run. In these reactions isoprene was treated with concentrated hydrochloric acid in a 2:1 mole ratio of 37% acid to isoprene in the presence of recycled byproducts comprising heads and tails fractions from previous distillations along with the intermittent and concurrent addition of sodium chloride. The reaction conditions which were employed were similar in nature to those set forth in the above examples, the analysis being performed by means of gas-liquid chromatographic instruments on distilled fractions. The results of four runs are set forth in the table below:

| Run | Recycle Material | Sodium Chloride | ← Product Selectivity % → | | | | Isoprene Conversion Mole % |
| | | | 3-Chloro-3-methyl-butene-1 | Dichloro-methyl-butane | Heavies | Prenyl Chloride | |
| --- | --- | --- | --- | --- | --- | --- | --- |
| 1 | None | None | 8 | 4 | 5 | 79 | 86 |
| 2 | Yes | None | 2 | 3.5 | 4 | 85 | 85 |
| 3 | Yes | Yes | 3 | 1 | 4 | 87 | 87 |

-continued

| | | | ← Product Selectivity % → | | | | |
|---|---|---|---|---|---|---|---|
| Run | Recycle Material | Sodium Chloride | 3-Chloro-3-methyl-butene-1 | Dichloro-methyl-butane | Heavies | Prenyl Chloride | Isoprene Conversion Mole % |
| 4 | Yes | Yes | 1.4 | 2 | 2.5 | 89 | 86 |

It is therefore readily apparent from the above table that by repeatedly recycling the byproducts from a previous distillation plus the addition of sodium chloride along with hydrochloric acid, that an approximately steady state system is achieved with a decreased amount of unwanted byproducts present in the reaction mixture along with a concurrent increase in the yield of the desired product, namely, prenyl chloride.

EXAMPLE IV

The general procedure of Example I may be reported with the exception that calcium chloride is employed instead of sodium chloride to afford high yields and conversions of isoprene to prenyl chloride.

WE CLAIM AS OUR INVENTION:

1. A process for the preparation of prenyl chloride which comprises reacting isoprene with aqueous hydrochloric acid in the presence of an alkali metal chloride at reaction conditions, and recovering the resultant prenyl choride.

2. The process as set forth in claim 1 further characterized in that the reaction of isoprene which hydrochloric acid and an alkali metal chloride is further effected in the presence of byproduct heads and tails materials lighter and heavier than prenyl chloride from a previous similar reaction.

3. The process as set forth in claim 1 in which said reaction conditions include a temperature in the range of from about 0° to about 30° C.

4. The process as set forth in claim 1 in which said alkali metal chloride is sodium chloride.

5. The process as set forth in claim 1 in which said alkali metal chloride is potassium chloride.

6. The process as set forth in claim 1 in which said hydrochloric acid is concentrated hydrochloric acid of from about 32 to 37% hydrogen chloride.

7. The process as set forth in claim 1 in which said hydrochloric acid and alkali metal metal chloride are added in incremental portions.

8. The process as set forth in claim 7 which said hydrochloric acid and alkali metal metal chloride are admixed and added in a single stream.

9. The process as set forth in claim 1 in which said hydrochloric acid is present in a molar excess over said isoprene in a ratio of from about 1.1:1 to about 2.5:1 moles of hydrochloric acid per mole of isoprene.

* * * * *